Jan. 14, 1964 W. ELLERBROK Plant Pat. 2,341
BARBERRY PLANT
Filed Jan. 16, 1963
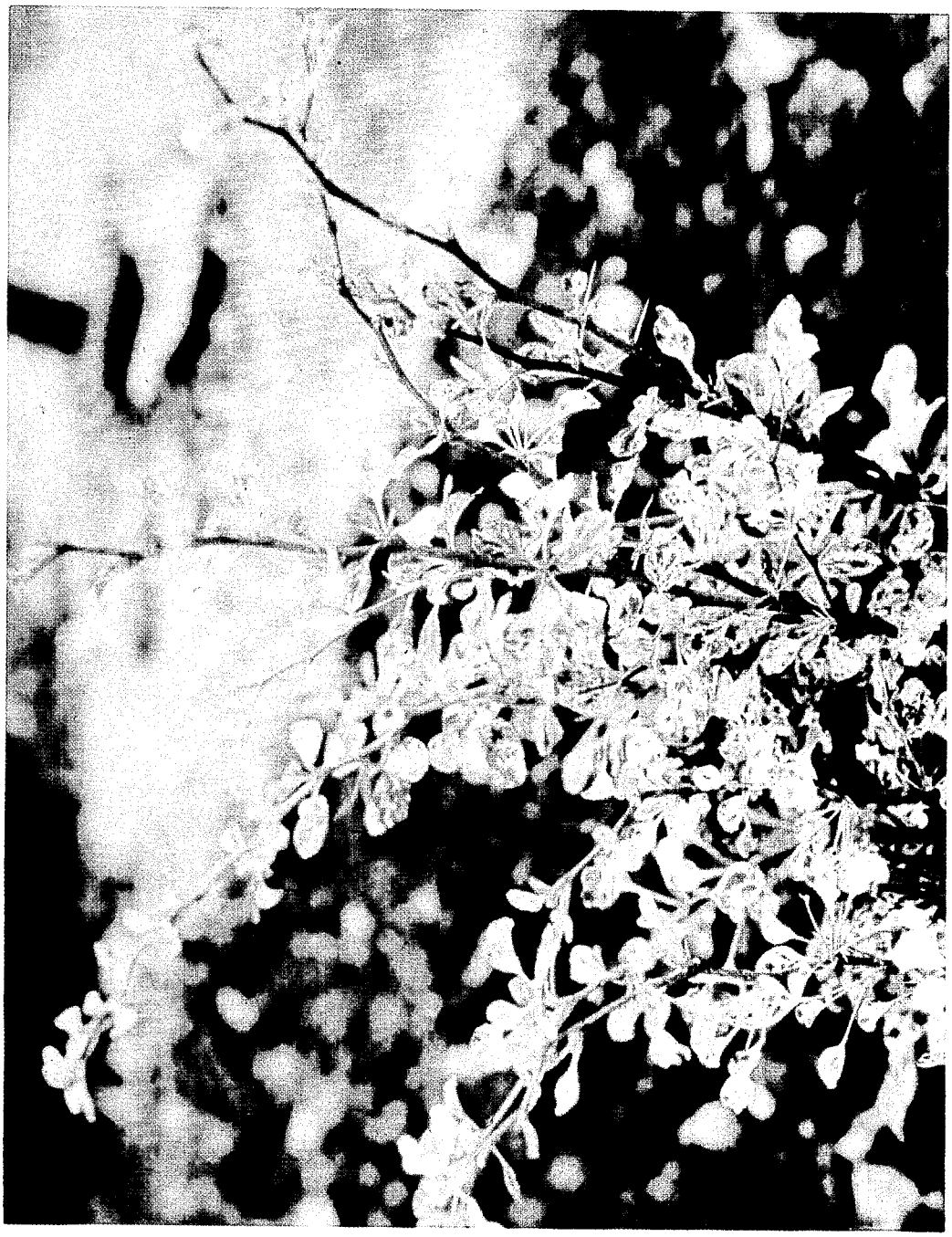
Inventor.
William Ellerbrok
By: Robb & Robb
Attorneys.

United States Patent Office

Plant Pat. 2,341
Patented Jan. 14, 1964

2,341
BARBERRY PLANT

William Ellerbrok, Sydney River, Nova Scotia, Canada

Filed Jan. 16, 1963, Ser. No. 251,994
1 Claim. (Cl. Plt.—58)

The present invention relates to a new and distinct variety of barberry plant which was originated by me by crossing an unnamed and unpatented variegated variety of *Berberis thunbergi* with an unnamed and unpatented barberry variety botanically known as *Berberis thunbergi atropurpurea,* the former being the seed parent and the latter being the pollen parent.

As the result of this breeding, I have produced a new barberry variety which is distinguished from its parents, as well as from all other varieties of which I am aware, by the following unique combination of characteristics which are outstanding therein and which make the new variety of great importance from a commercial standpoint:

(1) A dwarf habit of growth;

(2) Variegated foliage in which the variegated colors are principally red, white and light orange; and (3) Good hardiness, as evidenced by the fact that the new variety has withstood temperatures in Nova Scotia as low as 20 degrees below zero without damage or injury.

In comparison with its seed parent, the new variety has a dwarf habit of growth and does not grow as tall as the parent variety, and the variegated colors of the foliage are quite different as the result of combining the principal colors red, white and light orange, as contrasted with the usual green and white foliage of the parent variety, thus representing a very unique and highly attractive foliage color.

As compared with its pollen parent, the new variety is much lower growing in its habit by virtue of its characteristic dwarf habit, and the variegated foliage colors are quite different from the normal deep red or purple foliage color of this parent variety.

Asexual reproduction of my new variety by cuttings, as performed by me at Sydney River, Nova Scotia, Canada, shows that the foregoing characteristis and distinctions come true to form and are transmissible through succeeding propagations.

The accompanying drawing shows a typical specimen plant of my new barberry variety, with the branches and foliage depicted in color as nearly true as it is reasonably possible to make the same in a color illustration of this character.

The following is a detailed description of the new variety, with color terminology in accordance with Nickerson's Color Fan, published by Munsell Color Company, Incorporated, of Baltimore, Maryland, except where general color terms of ordinary dictionary significance are obvious, and as based upon specimens grown outdoors at Sydney River, Nova Scotia, Canada:

Parentage: Seedling.

*Seed parent.*—*Berberis thunbergi* (variegated form).

*Pollen parent.*—*Berberis thunbergi atropurpurea.*

Propagation: Holds its distinguishing characteristics through succeeding propagations by cuttings.

*Plant*

Growth: Dwarf; upright-spreading; dense; hardy.

Wood: Stocky.

*New wood.*—Color—Strong Red, Plate 5R 4/12.

*Mature wood.*—Color—Moderate Reddish Brown, Plate 2.5YR 3/3.

Foliage:

*Leaves.*—Quantity—normal quantity comparable to the variety botanically known as *Berberis thunbergi.* Size (when mature): length—about ¾ inch; width—about ½ inch. Shape—oval. Thickness—thin. Margin—smooth edge. Petiole—medium length. Glands—none. Stipules—none. Color: new foliage—variegations of ivory, Light Orange, Plate 2.5YR 8/6, and Moderate Reddish Brown, Plate 7.5YR 3/6, with the ivory color extending over the major portion of the leaves. Mature foliage—variegations of ivory white, Pale Orange Yellow, Plate 7.5YR 9/4, Moderate Yellowish Pink, Plate 10R 8/6, Moderate Pink, Plate 5R 8/6, and Grayish Olive Green, Plate 5GY 3/2, with the ivory white color predominating.

Flowers: None produced or observed to date.

Fruit: None produced or observed to date.

I claim:

A new and distinct variety of barberry plant, substantially as herein shown and described, characterized particularly as to novelty by the unique combination of a dwarf habit of growth, distinctive and attractive foliage of variegated colors, with white, light orange and red colors predominating, and good hardiness.

No references cited.